(12) United States Patent
Igarashi

(10) Patent No.: US 10,940,260 B2
(45) Date of Patent: Mar. 9, 2021

(54) BLOOD COMPONENT SEPARATION DEVICE AND BLOOD COMPONENT SEPARATION METHOD

(71) Applicant: TERUMO KABUSHIKI KAISHA, Tokyo (JP)

(72) Inventor: Masatsugu Igarashi, Tokyo (JP)

(73) Assignee: Terumo Kabushiki Kaisha, Tokyo (JP)

( * ) Notice: Subject to any disclaimer, the term of this patent is extended or adjusted under 35 U.S.C. 154(b) by 166 days.

(21) Appl. No.: 16/086,259

(22) PCT Filed: Mar. 13, 2017

(86) PCT No.: PCT/JP2017/009886
§ 371 (c)(1),
(2) Date: Sep. 18, 2018

(87) PCT Pub. No.: WO2017/163956
PCT Pub. Date: Sep. 28, 2017

(65) Prior Publication Data
US 2019/0344008 A1    Nov. 14, 2019

(30) Foreign Application Priority Data

Mar. 21, 2016   (JP) .................................. 2016-056381

(51) Int. Cl.
*B01D 21/26*   (2006.01)
*A61M 1/36*    (2006.01)
(Continued)

(52) U.S. Cl.
CPC ........ *A61M 1/3683* (2014.02); *A61M 1/3604* (2014.02); *A61M 1/3672* (2013.01);
(Continued)

(58) Field of Classification Search
CPC .... A61M 1/38; A61M 1/3672; A61M 1/3681; A61M 1/0209; A61M 1/0272;
(Continued)

(56) References Cited

U.S. PATENT DOCUMENTS

2012/0094269 A1    4/2012  Wieland et al.
2012/0252001 A1*  10/2012  Shaz ................... C12N 5/0644
                                                         435/2
(Continued)

FOREIGN PATENT DOCUMENTS

EP     1972354 A1 *   9/2008  .......... A61M 1/0236
EP     1972354 A1     9/2008

OTHER PUBLICATIONS

International Searching Authority, International Search Report, PCT/JP2017/009886, dated May 30, 2017, 2 pages.

*Primary Examiner* — Cameron J Allen
(74) *Attorney, Agent, or Firm* — Terumo BCT, Inc IP Law Dept

(57) ABSTRACT

Provided is a blood component separation device and related method, each capable of separating a blood component from blood and rapidly performing a virus inactivation process on the separated blood component. The blood component separation device includes a blood component separation section, provided in a centrifuge, configured to separate a blood component from blood by centrifugation, a diluting section configured to dilute, in a diluent containing riboflavin, concentrated red blood cells separated by the blood component separation section, and a UV light emitting unit configured to perform a virus inactivation process by exposing the concentrated red blood cells thus diluted to the UV light.

12 Claims, 11 Drawing Sheets

(51) Int. Cl.
 *B01D 36/04* (2006.01)
 *B04B 5/04* (2006.01)
(52) U.S. Cl.
 CPC ......... *A61M 1/3693* (2013.01); *B01D 21/262* (2013.01); *B01D 36/045* (2013.01); *B04B 5/0442* (2013.01); *A61M 2202/0415* (2013.01); *A61M 2202/0427* (2013.01); *A61M 2202/0429* (2013.01); *A61M 2202/206* (2013.01)
(58) Field of Classification Search
 CPC .............. A61M 1/3693; A61M 1/3683; A61M 1/3604; A61M 2202/0429; A61M 2202/206; A61M 2202/0415; A61M 2202/0427; B04B 5/0442; B01D 21/262; B01D 36/045
 See application file for complete search history.

(56) References Cited

U.S. PATENT DOCUMENTS

2015/0359959 A1\* 12/2015 Radwanski ......... A61M 1/3693
 210/748.11
2019/0321408 A1\* 10/2019 Gooris ................ C12N 5/0644

\* cited by examiner

BLOOD COMPONENT SEPARATION DEVICE AND BLOOD COMPONENT SEPARATION METHOD

TECHNICAL FIELD

The present disclosure relates to a blood component separation device and a blood component separation method each for separating a blood component from blood and collecting the blood component.

BACKGROUND ART

Patent Literature 1 discloses a blood component separation device for separating a plurality of blood components from blood and collecting the plurality of blood components.

CITATION LIST

Patent Literature

PTL 1: U.S. Patent Application No. 2007/0282242

SUMMARY OF INVENTION

Technical Problem

In order to take a sufficient measure against viruses transmitted by blood, a process of inactivating viruses contained in various blood products (whole blood, concentrated red blood cells, platelets, plasma) produced from blood collected from a blood donor is performed. For example, for a blood product collected with a blood component separation device as that disclosed by Patent Literature 1, a process (virus inactivation process) of emitting UV light (ultraviolet light) to the blood product to inactivate viruses in the blood product is performed. However, in order to manufacture such blood products in which viruses are inactivated, it has taken much time. This is because it has been necessary to first perform centrifugation by use of the blood component separation device as that disclosed by Patent Literature 1 to yield various blood components (concentrated red blood cells, platelets, plasma), and further to perform the virus inactivation process thereon. Especially, a blood product (whole blood, concentrated red blood cells) containing red blood cells might involve the following case. That is, since the red blood cells absorb or reflect UV light, the UV light can hardly be transmitted through the blood product. Consequently, only viruses in a surficial portion of the blood product are inactivated. In order to deal with this, for example, it has been necessary to emit the UV light to the blood product while stirring the blood product for moving the red blood cells. Thus, it has taken time to perform the process of inactivating viruses.

The present disclosure was made in order to solve the above-described problem. An object of the present disclosure is to provide a blood component separation device and a blood component separation method each capable of separating a blood component from blood and quickly performing a virus inactivation process on the blood component separated from the blood.

Solution To Problem

An aspect of the present invention to solve the problem is a blood component separation device including: a blood component separation section for separating a blood component from blood by centrifuging the blood, where the blood has been collected from a blood donor; a diluting section for diluting, in a diluent containing a photoactive virus inactivation agent, the blood component separated by the blood component separation section; and a blood-component virus inactivation section for performing a virus inactivation process by emitting light to the diluted blood component.

According to the above aspect, the blood component is separated from the blood, and then the blood component is diluted in the diluent containing the photoactive virus inactivation agent, so that a concentration of the blood component is reduced. This makes it easier for the photoactive virus inactivation agent to be irradiated with the light, when the light is emitted to the blood component. This enhances efficiency in the process of inactivating the viruses in the blood component. This makes it possible to quickly perform the virus inactivation process on the blood component separated from the blood.

In the above aspect, it is preferable that a concentration adjustment section for adjusting a concentration of the blood component having been subjected to the virus inactivation process is included.

According to the above aspect, the blood component that has been once diluted to a lower concentration can be collected after adjusted to a desired concentration.

In the above aspect, it is preferable that the concentration adjustment section adjusts the concentration of the blood component by centrifuging the blood component.

According to the above aspect, a centrifugal force is applied to the blood component having been diluted, so that the diluent is separated and removed therefrom. Thus, it is possible to easily collect the blood component having a desired concentration.

In the above aspect, it is preferable that the blood component separation section and the concentration adjustment section are provided in a single centrifugal separation device.

According to the above aspect, the process of separating the blood component and the process of adjusting the concentration of the blood component can be performed at once. This reduces time taken to collect, from the blood, the blood component having a desired concentration. Furthermore, this allows the blood component separation device to be downsized.

In the above aspect, it is preferable that the blood component separation section and the concentration adjustment section are provided in an identical centrifugal separation section.

According to the above aspect, the process of separating the blood component and the process of adjusting the concentration of the blood component can be performed at once in the identical centrifugal separation section. This further reduces time taken to collect, from the blood, the blood component having a desired concentration. Furthermore, this allows the blood component separation device to be further downsized.

In the above aspect, it is preferable that the concentration adjustment section includes a filter, and the concentration of the blood component is adjusted by guiding the blood component to the filter so that the blood component is caught by the filter, and then flowing a liquid component to the filter in an opposite direction so that the blood component caught by the filter is collected.

According to the above aspect, the blood component that has been once diluted to a lower concentration can be collected after adjusted to a desired concentration.

In the above aspect, it is preferable that the blood component is concentrated red blood cells.

According to the above aspect, it is possible to quickly perform the virus inactivation process on the concentrated red blood cells separated from the blood.

In the above aspect, it is preferable that the blood component is platelets.

According to the above aspect, it is possible to quickly perform the virus inactivation process on the platelets separated from the blood.

In the above aspect, it is preferable that at least one of: a plasma virus inactivation section for performing a virus inactivation process on plasma separated by the blood component separation section; and a platelet virus inactivation section for performing a virus inactivation process on platelets separated by the blood component separation section, is included.

According to the above aspect, it is possible to collect the plasma and the platelets having been subjected to the virus inactivation process, in addition to the concentrated red blood cells having been subjected to the virus inactivation process.

Another aspect of the present invention to solve the problem is a blood component separation method including: blood component separating step of separating a blood component from blood by centrifuging the blood, where the blood has been collected from a blood donor; diluting step of diluting, in a diluent containing a photoactive virus inactivation agent, the blood component separated in the blood component separating step; and virus inactivation step of performing a virus inactivation process by emitting light to the diluted blood component.

According to the above aspect, the blood component is separated from the blood, and then the blood component is diluted in the diluent containing the photoactive virus inactivation agent, so that a concentration of the blood component is reduced. This makes it easier for the photoactive virus inactivation agent to be irradiated with the light, when the light is emitted to the blood component. This enhances efficiency in the process of inactivating the viruses in the blood component. Therefore, it is possible to quickly perform the virus inactivation process on the blood component separated from the blood.

Advantageous Effects of Invention

With each of a blood component separation device and a blood component separation method according to an aspect of the present disclosure, it is possible to separate a blood component from blood and to quickly perform a virus inactivation process on the blood component separated from the blood.

DESCRIPTION OF EMBODIMENTS

Figure 1:
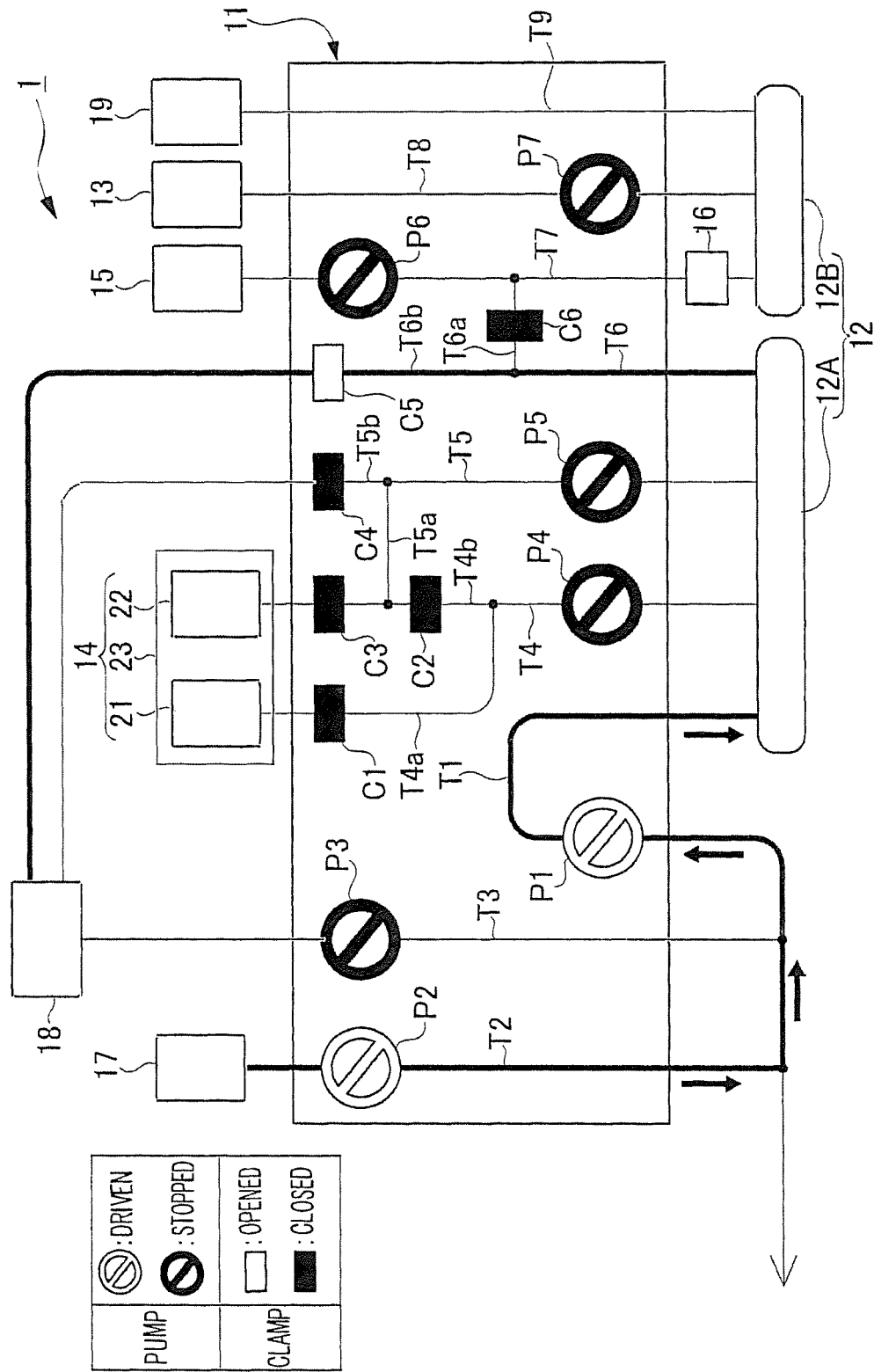
FIG. 1 is a view schematically illustrating a configuration of a blood component separation device according to an embodiment of the present disclosure, and shows a step of priming.

As shown in FIG. 1, a blood component separation device 1 according an embodiment of the present disclosure includes elements such as a cassette 11, a centrifuge 12, a red blood cell collecting bag 13, a plasma and platelet collecting section 14, a diluent storing section 15, a UV emitting unit 16 (a blood-component virus inactivation section, a red-blood-cell virus inactivation section), an anticoagulant bag 17, a reservoir 18, and a fluid waste bag 19.

The cassette 11 includes a plurality of paths, specifically, a whole blood path T1, an anticoagulant path T2, a blood returning path T3, a plasma path T4, a platelet path T5, a first red blood cell path T6, a diluting path T7, a second red blood cell path T8, and a fluid waste path T9.

The whole blood path T1 is connected to a blood collection needle (not illustrated), with which whole blood (blood) is collected from a blood donor (donor), and to an inflow line 33 (see FIG. 2) of the blood component separation section 12A of the centrifuge 12. The anticoagulant path T2 is connected to the anticoagulant bag 17 and to the whole blood path T1. The blood returning path T3 is connected to the reservoir 18 and to the whole blood path T1.

The plasma path T4 is connected to a plasma line 38 (see FIG. 2) of the blood component separation section 12A. The plasma path T4 includes a first branched path T4a and a second branched path T4b, which are branched from the plasma path T4. The first branched path T4a is connected to a plasma collecting bag 21. The second branched path T4b is connected to a first branched path T5a of the platelet path T5. Through the plasma path T4, plasma separated by the blood component separation section 12A flows.

The platelet path T5 is connected to a platelet line 37 (see FIG. 2) of the blood component separation section 12A. The platelet path T5 includes the first branched path T5a and a second branched path T5b, which are branched from the platelet path T5. The first branched path T5a is connected to a platelet collecting bag 22. The second branched path T5b is connected to the reservoir 18. Through the platelet path T5, platelets separated by the blood component separation section 12A flow.

The first red blood cell path T6 is connected to a first red blood cell line 34 (see FIG. 2) of the blood component separation section 12A. The first red blood cell path T6 includes a first branched path T6a and a second branched path T6b, which are branched from the first red blood cell path T6. The first branched path T6a is connected to the diluting path T7. The second branched path T6b is connected to the reservoir 18. Through the first red blood cell path T6, concentrated red blood cells that are separated by the blood component separation section 12A and are not yet diluted in the diluting path T7 flow.

The diluting path T7 is connected to the diluent storing section 15 and to an inflow line 52 (see FIG. 2) of a condenser 12B of the centrifuge 12. Through the diluting path T7, a diluent containing riboflavin (described later) or concentrated red blood cells diluted in the diluent flow.

The second red blood cell path T8 is connected to a second red blood cell line 53 (see FIG. 2) of the condenser 12B and to the red blood cell collecting bag 13. Through the second red blood cell path T8, concentrated red blood cells resulting from condensation by the condenser 12B, i.e., a concentration adjustment by the condenser 12B, flow.

The fluid waste path T9 is connected to a fluid waste line 54 (see FIG. 2) of the condenser 12B and to the fluid waste bag 19.

The cassette 11 includes a plurality of pumps, specifically, a first pump P1 to a seventh pump P7. The first pump P1 is disposed in the whole blood path T1, the second pump P2 is disposed in the anticoagulant path T2, the third pump P3 is disposed in the blood returning path T3, the fourth pump P4 is disposed in the plasma path T4, the fifth pump P5 is disposed in the platelet path T5, the sixth pump P6 is disposed in the diluting path T7, and the seventh pump P7 is disposed in the second red blood cell path T8.

The cassette 11 includes a plurality of clamps, specifically, a first clamp C1 to a sixth clamp C6 for opening and closing the paths. The first clamp C1 is disposed in the first branched path T4a of the plasma path T4, the second clamp C2 is disposed in the second branched path T4b of the plasma path T4, the third clamp C3 is disposed in the first branched path T5a of the platelet path T5, the fourth clamp C4 is disposed in the second branched path T5b of the platelet path T5, the fifth clamp C5 is disposed in the second branched path T6b of the first red blood cell path T6, and the sixth clamp C6 is disposed in the first branched path T6a of the first red blood cell path T6.

Figure 2:
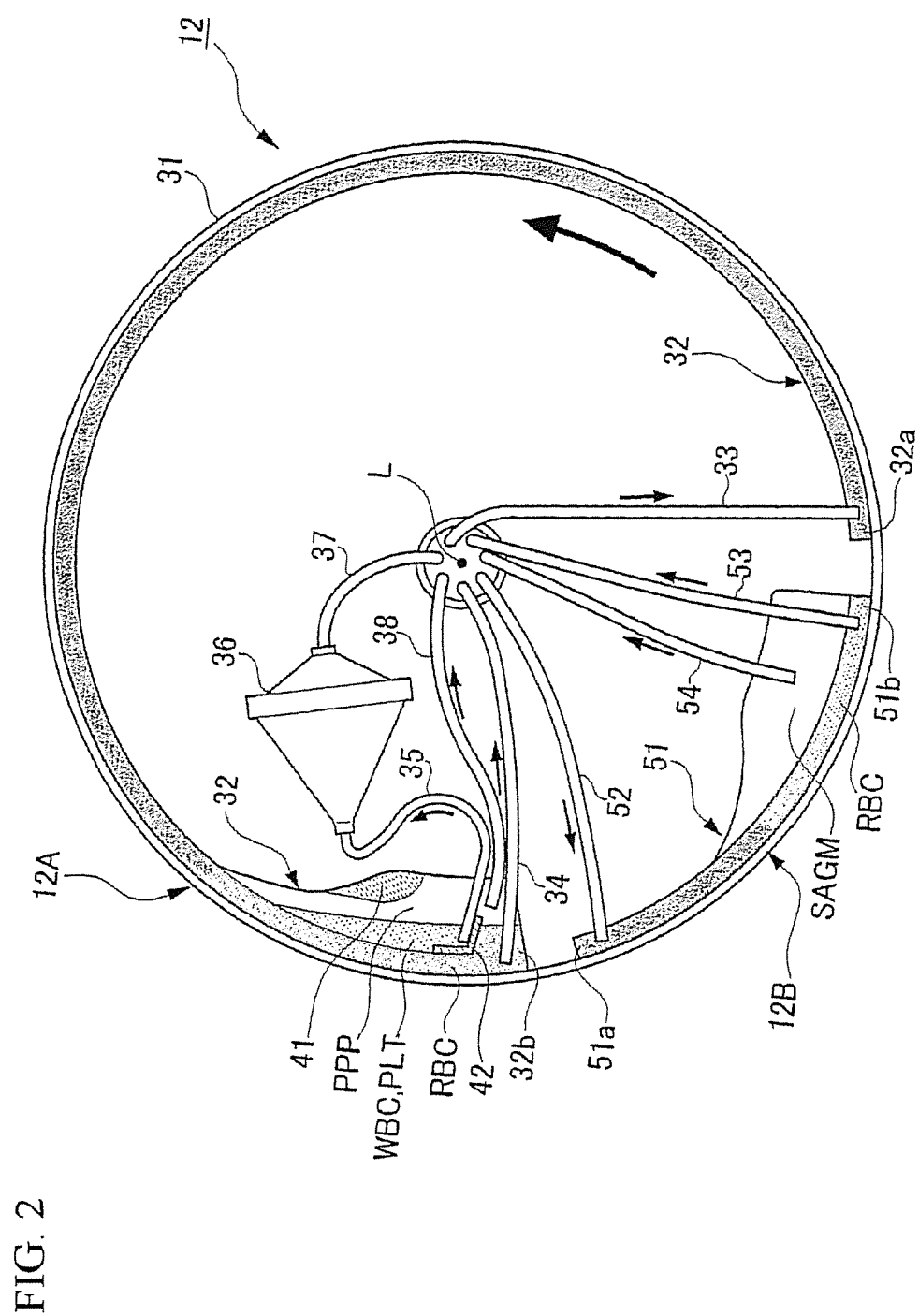
FIG. 2 is a view illustrating a configuration of a centrifuge.

As shown in FIGS. 1 and 2, the centrifuge 12 is a centrifugal separation device including the blood component separation section 12A and the condenser 12B (concentration adjustment section). As such, the blood component separation section 12A and the condenser 12B are included in the single centrifuge 12. The blood component separation section 12A centrifuges blood collected from a blood donor to separate a plurality of blood components from the blood. The condenser 12B adjusts a concentration of concentrated red blood cells having been subjected to the virus inactivation process (the process of inactivating the viruses in the concentrated red blood cells). According to the present embodiment, the condenser 12B adjusts the concentration of the concentrated red blood cells by centrifuging the concentrated red blood cells. The centrifuge 12 will be described in detail later.

The red blood cell collecting bag 13 is connected to the second red blood cell path T8. The red blood cell collecting bag 13 preliminarily contains a red blood cell preservation solution. As will be described later, the red blood cell collecting bag 13 collects the concentrated red blood cells that have been subjected to the virus inactivation process performed by the UV emitting unit 16 and have been adjusted to a desired concentration by the condenser 12B.

The plasma and platelet collecting section 14 includes the plasma collecting bag 21, the platelet collecting bag 22, and a UV emitting unit 23 (a plasma virus inactivation section, a platelet virus inactivation section). The plasma collecting bag 21 and the platelet collecting bag 22 are located inside the UV emitting unit 23. Note that the plasma collecting bag 21 and the platelet collecting bag 22 are removable from the UV emitting unit 23.

The plasma collecting bag 21 is connected to the first branched path T4a of the plasma path T4. The plasma collecting bag 21 preliminarily contains a preservation solution containing riboflavin (photoactive virus inactivation agent). As will be described later, the plasma collecting bag 21 collects plasma that has been separated from the blood by the blood component separation section 12A of the centrifuge 12.

The platelet collecting bag 22 is connected to the first branched path T5a of the platelet path T5. The platelet collecting bag 22 preliminarily contains a preservation solution containing riboflavin. As will be described later, the platelet collecting bag 22 collects platelets that have been separated from the blood by the blood component separation section 12A of the centrifuge 12.

The UV emitting unit 23 is configured so as to accommodate, in its inside, the plasma collecting bag 21 and the platelet collecting bag 22. The UV emitting unit 23 includes a UV emitting element (not illustrated). As will be described later, the UV emitting unit 23 performs the virus inactivation process by causing the UV emitting element to emit UV light to the plasma collected in the plasma collecting bag 21 and the platelets collected in the platelet collecting bag 22.

The diluent storing section 15 is connected to the diluting path T7. The diluent storing section 15 stores, in its inside, the diluent containing riboflavin. The diluent containing riboflavin is preferably a mixture of a red blood cell preservation solution and a riboflavin solution. In the present embodiment, the diluent storing section 15, the diluting path T7, and the sixth pump P6 constitute a diluting section that dilutes, in the diluent containing riboflavin, concentrated red blood cells separated by the blood component separation section 12A. Instead of riboflavin, the photoactive virus inactivation agent may be an alkylating agent and/or glutathione (GSH, γ-glutamyl-rcysteinyl-glycine).

The UV emitting unit 16 is disposed in the diluting path T7. The UV emitting unit 16 includes a UV emitting element (not illustrated). The UV emitting unit 16 performs the virus inactivation process or one or more pathogens reduction by causing the UV emitting element to emit UV light to the concentrated red blood cells diluted in the diluent containing riboflavin.

According to the present embodiment, the UV emitting unit 16 includes the flow path (the diluting path T7) through which the concentrated red blood cells are to be flown, and the flow path is configured to have a long length. This leads to a long residence time of the concentrated red blood cells in the UV emitting unit 16. Furthermore, the flow path through which the concentrated red blood cells are to be flown has a low height. Moreover, the flow path through which the concentrated red blood cells are to be flown is provided with a plurality of UV emitting elements that is disposed on both sides of the flow path and is arranged in an axial direction of the flow path, where both the sides are along a height direction of the flow path. Such a configuration allows the concentrated red blood cells to have a large surface area that can be irradiated with the UV light, and leads to long time to emit the UV light to the concentrated red blood cells. This enhances efficiency in the virus inactivation process. Accordingly, it is possible to reduce time taken to perform the virus inactivation process.

The anticoagulant bag 17 is connected to the anticoagulant path T2. The anticoagulant bag 17 stores, in its inside, an ACD solution as an anticoagulant for retarding coagulation of blood. The reservoir 18 is connected to the second branched path T5b of the platelet path T5, to the second branched path T6b of the first red blood cell path T6, and to the blood returning path T3. The fluid waste bag 19 is connected to the fluid waste path T9. The fluid waste bag 19 collects, as fluid waste, the red blood cell preservation solution that is sent from the condenser 12B through the fluid waste path T9.

Next, the centrifuge 12 will be explained. As shown in FIG. 2, the centrifuge 12 includes a centrifuge unit 31 having a circular outer circumference. The centrifuge unit 31 is driven by a motor (not illustrated) so as to be rotated about a central axis L. The centrifuge 12 includes the blood component separation section 12A and the condenser 12B such that the blood component separation section 12A and the condenser 12B are located inside the centrifuge unit 31.

The blood component separation section 12A includes elements such as a flow path 32, the inflow line 33, the first red blood cell line 34, a platelet and while blood cell line 35, a chamber 36, the platelet line 37, and the plasma line 38.

The flow path 32 has an arc-shaped outer circumference, and extends along a circumferential direction of the centrifuge unit 31. The flow path 32 includes an inlet 32a and an accumulation chamber 32b. The inlet 32a is one end of the flow path 32 along the circumferential direction, and allows the incoming blood to flow therethrough. The accumulation chamber 32b is the other end of the flow path 32 along the circumferential direction, and accumulates the separated blood components therein. Note that the accumulation chamber 32b is formed so as to protrude more inwardly than the inlet 32a, so that the accumulation chamber 32b has a large area serving as a flow path.

The inflow line 33 is connected to the whole blood path T1 (see FIG. 1) of the cassette 11 and to the inlet 32a of the flow path 32. The first red blood cell line 34 is connected to the accumulation chamber 32b of the flow path 32 and to the first red blood cell path T6 (see FIG. 1) of the cassette 11. The platelet and while blood cell line 35 is connected to the accumulation chamber 32b of the flow path 32 and to the chamber 36. The platelet line 37 is connected to the chamber 36 and to the platelet path T5 (see FIG. 1) of the cassette 11. The plasma line 38 is connected to the accumulation chamber 32b of the flow path 32 and to the plasma path T4 (see FIG. 1) of the cassette 11.

In the blood component separation section 12A configured as above, first, the flow path 32 is filled with blood collected from a blood donor. Specifically, as shown in FIG. 2, the blood flows through the inflow line 33, which is connected to the whole blood path T1, and then flows into the flow path 32. In the flow path 32, the blood flows from the inlet 32a to the accumulation chamber 32b in a counterclockwise direction (i.e., around to the left).

Then, the centrifuge unit 31 is driven so as to be rotated. Consequently, due to a centrifugal force, the blood is separated into components in a position upstream of an innerwall dam 41, which is formed in the accumulation chamber 32b of the flow path 32, as shown in FIG. 2. As a result, the components of the blood are layered from the outer periphery of the centrifuge unit 31 inwardly in a descending order of density, namely, in the order of red blood cells RBC, white blood cells WBC, platelets PLT, and plasma PPP. That is to say, as shown in FIG. 2, a layer of the red blood cells RBC is formed along an outer wall of the flow path 32, and a layer of the plasma PPP is formed along an inner wall of the flow path 32. A layer of the platelets PLT and the white blood cells WBC is formed between the layer of the red blood cells RBC and the layer of the plasma PPP.

The red blood cells RBC (concentrated red blood cells) then flow to a position downstream of a skimmer dam 42, which is formed in the accumulation chamber 32b of the flow path 32 and has an L-shape. The red blood cells RBC then flow through the first red blood cell line 34 to the outside of the blood component separation section 12A, namely, to the first red blood cell path T6 (see FIG. 1).

The plasma PPP flows to a position upstream of the skimmer dam 42, and flows through the plasma line 38 to the outside of the blood component separation section 12A, namely, to the plasma path T4 (see FIG. 1).

The platelets PLT and the white blood cells WBC stay in a position upstream of the skimmer dam 42. After staying in the position, the platelets PLT and the white blood cells WBC flow through the platelet and while blood cell line 35 into the chamber 36. In the chamber 36, the white blood cells WBC are removed. Meanwhile, the platelets PLT flow through the platelet line 37 to the outside of the blood component separation section 12A, namely, to the platelet path T5 (see FIG. 1).

In this way, the blood component separation section 12A centrifuges the blood collected from the blood donor, so that the plurality of blood components is separated from the blood.

The condenser 12B includes elements such as a flow path 51, the inflow line 52, the second red blood cell line 53, and the fluid waste line 54.

The flow path 51 has an arc-shaped outer circumference, and extends along the circumferential direction of the centrifuge unit 31. The flow path 51 includes an inlet 51a and an accumulation chamber 51b. The inlet 51a is one end of the flow path 51 along the circumferential direction, and allows the incoming blood to flow therethrough. The accumulation chamber 51b is the other end of the flow path 51 along the circumferential direction, and accumulates, in its inside, the concentrated red blood cells resulting from the separation and the red blood cell preservation solution. Note that the accumulation chamber 51b is formed so as to protrude more inwardly than the inlet 51a, so that the accumulation chamber 51b achieves a large area serving as a flow path. In the example shown in FIG. 2, the flow path 51 has a shorter length than the flow path 32 of the blood component separation section 12A in the circumferential direction.

The inflow line 52 is connected to the diluting path T7 (see FIG. 1) of the cassette 11 and to the inlet 51a of the flow path 51. The second red blood cell line 53 is connected to the accumulation chamber 51b of the flow path 51 and to the second red blood cell path T8 (see FIG. 1) of the cassette 11. The fluid waste line 54 is connected to the accumulation chamber 51b of the flow path 51 and to the fluid waste path T9 (see FIG. 1) of the cassette 11.

In the condenser 12B configured as above, first, the flow path 51 is filled with the concentrated red blood cells (concentrated red blood cells diluted in a diluent (a red blood cell preservation solution SAGM)) having been subjected to the virus inactivation process performed by the UV emitting unit 16 (described in detail later). Specifically, as shown in FIG. 2, the concentrated red blood cells flow through the inflow line 52, which is connected to the diluting path T7, and then flows into the flow path 51. In the flow path 51, the concentrated red blood cells flow from the inlet 51a to the accumulation chamber 51b in the counterclockwise direction (i.e., around to the left).

Then, the centrifuge unit 31 is driven so as to be rotated. Consequently, due to a centrifugal force, the concentrated red blood cells are separated into components in the accumulation chamber 51b of the flow path 51, as shown in FIG. 2. As a result, the components of the concentrated red blood cells are layered from the outer periphery of the centrifuge unit 31 inwardly in the order of red blood cells RBC (concentrated red blood cells condensed to have an adjusted concentration) and the red blood cell preservation solution SAGM (diluent). Namely, as shown in FIG. 2, the layer of the red blood cells RBC is formed along an outer wall of the flow path 51, and the layer of the red blood cell preservation solution SAGM is formed along an inner wall of the flow path 51.

The red blood cells RBC (concentrated red blood cells condensed to have an adjusted concentration) flow through the second red blood cell line 53 to the outside of the condenser 12B, namely, to the second red blood cell path T8 (see FIG. 1).

The red blood cell preservation solution SAGM flows through the fluid waste line 54 to the outside of the condenser 12B, namely, to the fluid waste path T9 (see FIG. 1).

In this way, the condenser 12B centrifuges the concentrated red blood cells having been subjected to the virus inactivation process, so as to adjust the concentration of the concentrated red blood cells.

In the example shown in FIG. 2, the blood component separation section 12A and the condenser 12B are arranged side by side separated from each other by a distance along the circumferential direction of the centrifuge unit 31. However, the present disclosure is not limited to such a configuration. Alternatively, a blood component separation section 12A and a condenser 12B may be arranged so as to be in contact with each other, and a flow path 32 and a flow path 51 may be separated from each other by a wall.

Figure 13:
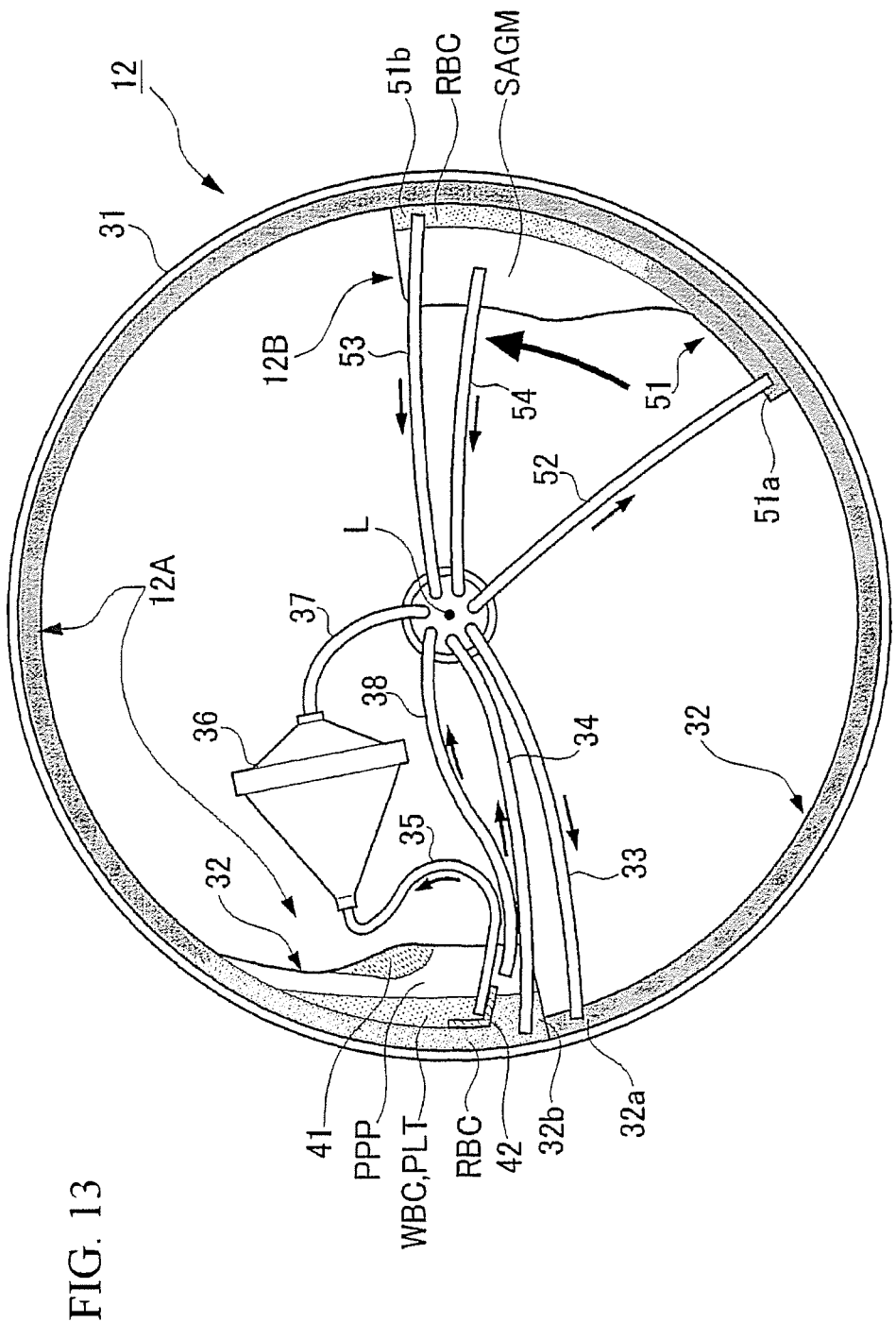
FIG. 13 is a view illustrating a configuration of a centrifuge according to a variation.

Further alternatively, the centrifuge 12 may be configured as shown in FIG. 13. In a centrifuge 12 shown in FIG. 13, a condenser 12B is arranged inwardly than a blood component separation section 12A in a radial direction of a centrifuge unit 31. Furthermore, an accumulation chamber 32b of a flow path 32 of the blood component separation section 12A and an accumulation chamber 51b of a flow path 51 of the condenser 12B are arranged so as to substantially face each other across a central axis L. The description so far concerns the centrifuge 12.

Next, the following describes an operation of the blood component separation device 1 configured as above. Note that the below-described operation of the blood component separation device 1 is controlled by a control section (not illustrated) included in the blood component separation device 1.

First, a step of priming is performed. Specifically, as shown in FIG. 1, the fifth clamp C5 is opened to drive the first pump P1 and the second pump P2, so that an ACD solution is flown from the anticoagulant bag 17 to the whole blood path T1 through the anticoagulant path T2. In this manner, the ACD solution is preliminarily adhered to parts that are to be in contact with blood, such as the whole blood path T1 and the blood component separation section 12A of the centrifuge 12, for the purpose of avoiding coagulation of the blood when the blood is flown.

Figure 3:
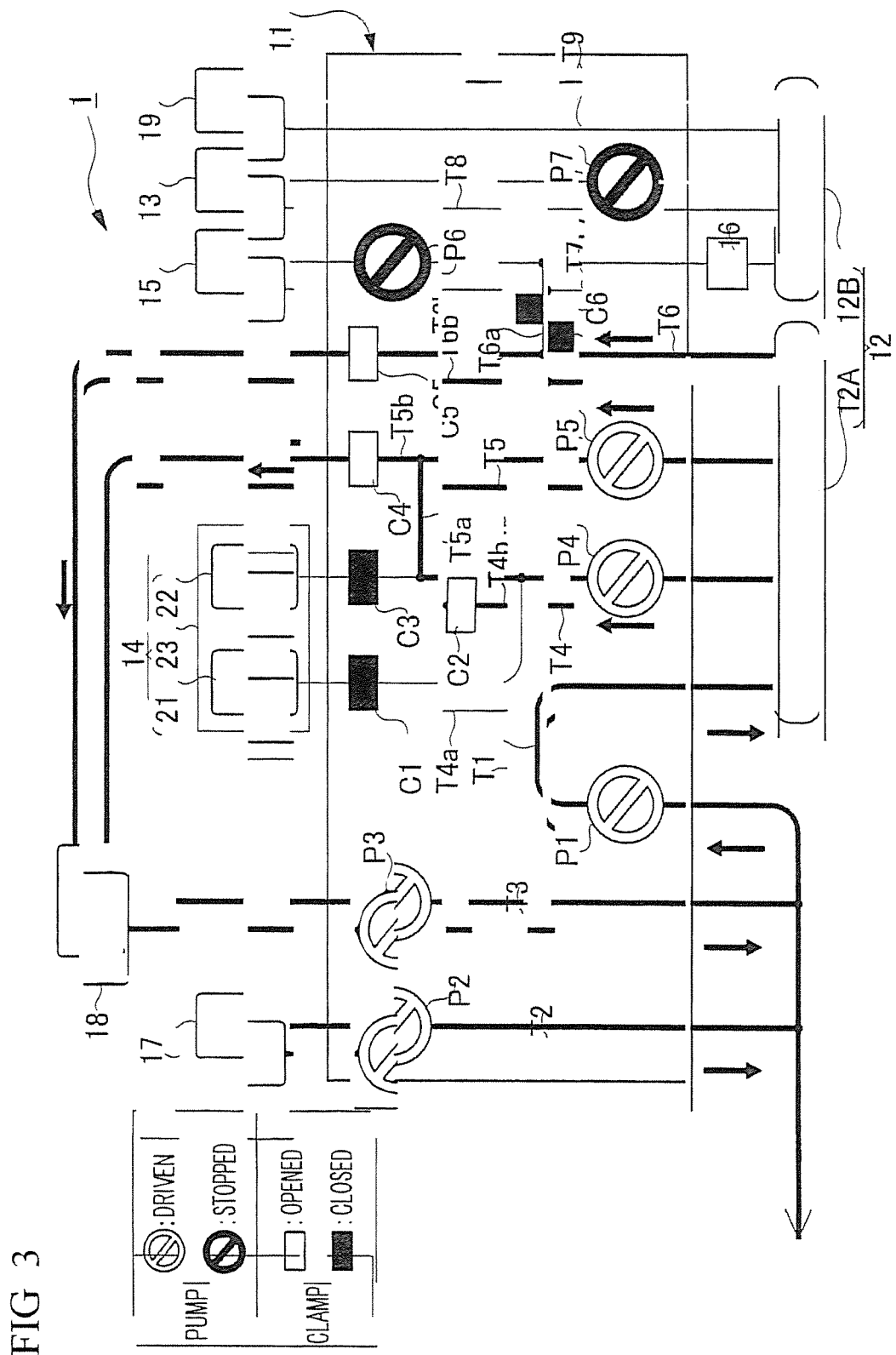
FIG. 3 is a view illustrating a step of starting blood collection and a step of preparing for collection.

Next, a step of starting blood collection is performed. Specifically, as shown in FIG. 3, blood collected from a blood donor is flown to the blood component separation section 12A of the centrifuge 12 through the whole blood path T1. In this manner, blood collection from the blood donor starts.

A step of preparing for collection is performed. Specifically, the blood component separation section 12A of the centrifuge 12 centrifuges the blood collected from the blood donor, so that a plurality of blood components is separated from the blood (a step of separating a blood component). In this manner, preparation for collection of the separated blood components is performed. To be more specific, as shown in FIG. 3, the second clamp C2, the fourth clamp C4, and the fifth clamp C5 are opened to drive the third pump P3, the fourth pump P4, and the fifth pump P5. Consequently, plasma from the blood component separation section 12A is flown into the reservoir 18 through the plasma path T4 (the second branched path T4b) and the platelet path T5 (the first branched path T5a and the second branched path T5b). Platelets from the blood component separation section 12A are flown into the reservoir 18 through the platelet path T5 (the second branched path T5b). Concentrated red blood cells from the blood component separation section 12A are flown into the reservoir 18 through the first red blood cell path T6 (the second branched path T6b). The blood components flown into the reservoir 18 are then flown into the blood returning path T3.

Figure 4:
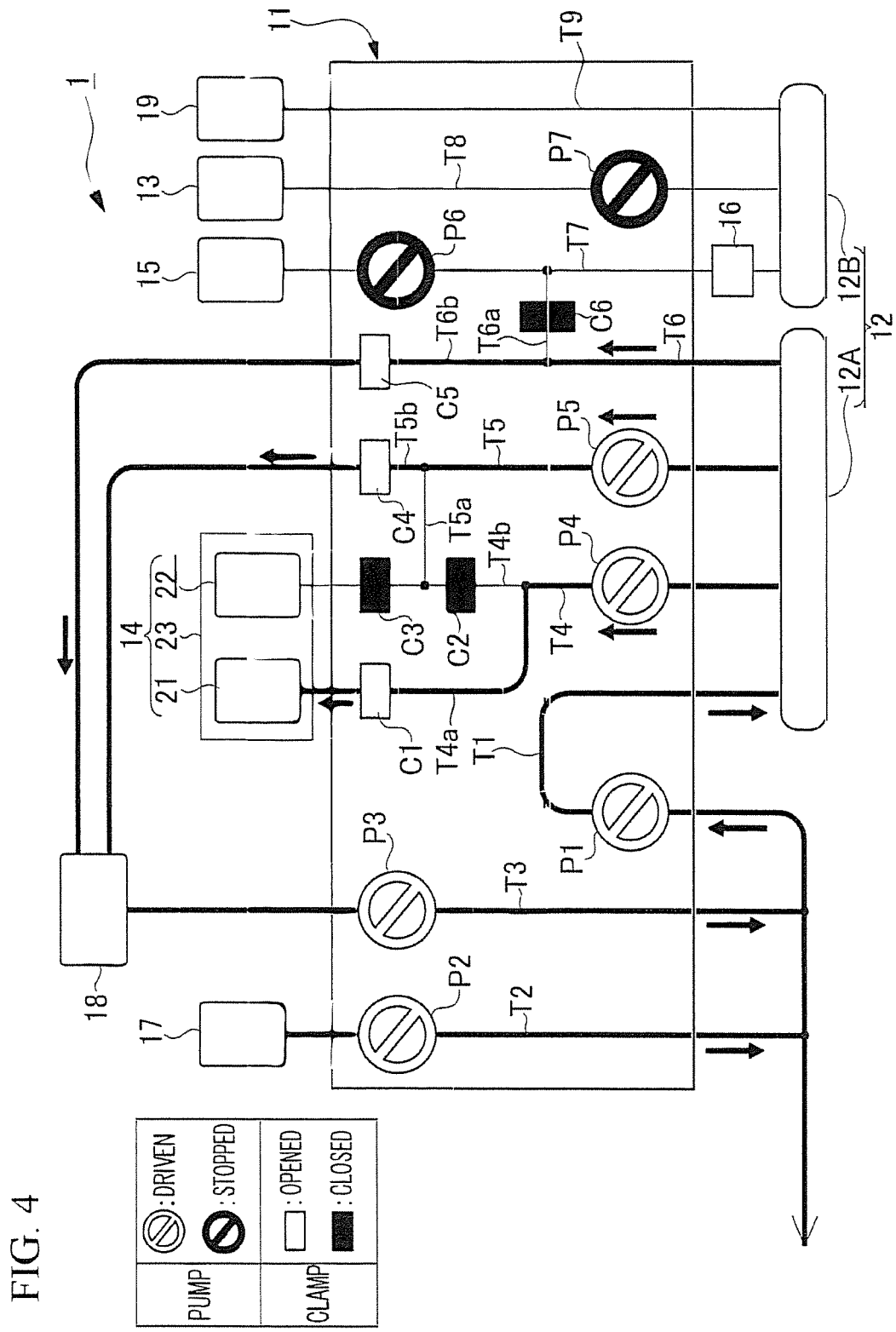
FIG. 4 is a view illustrating a step of collecting plasma and a step of emitting UV to the plasma.

Next, a step of collecting the plasma is performed. Specifically, as shown in FIG. 4, the second clamp C2 is closed, and the first clamp C1 is opened. Consequently, the plasma separated from the blood as a result of the centrifugation of the blood performed by the blood component separation section 12A of the centrifuge 12 is collected into the plasma collecting bag 21 through the plasma path T4 (the first branched path T4a).

A step of emitting UV to the plasma is performed. Specifically, the UV emitting unit 23 emits UV light to the plasma collected in the plasma collecting bag 21, so as to perform the virus inactivation process. This yields the plasma having been subjected to the virus inactivation process. Since the plasma collecting bag 21 preliminarily contains riboflavin as described above, the virus inactivation process can be performed effectively.

Figure 5:
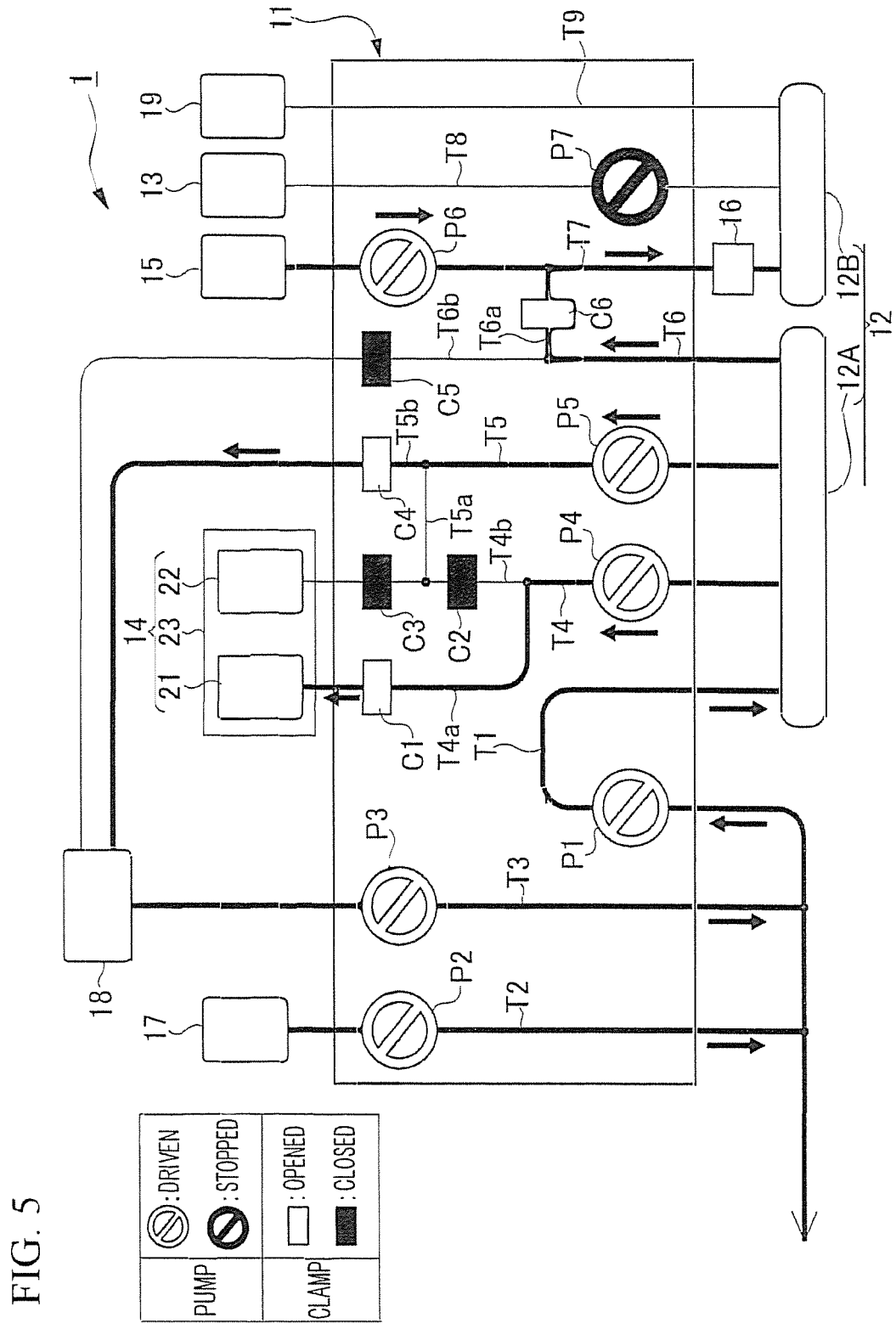
FIG. 5 is a view illustrating a step of collecting red blood cells, a step of diluting the red blood cells, and a step of emitting UV to the red blood cells, in addition to the steps shown in FIG. 4.

Next, a step of collecting red blood cells is performed. Specifically, as shown in FIG. 5, the fifth clamp C5 is closed, and the sixth clamp C6 is opened. Consequently, the concentrated red blood cells (the concentrated red blood cells separated in the step of separating the blood component) separated as a result of the centrifugation of the blood performed by the blood component separation section 12A of the centrifuge 12 are flown into the diluting path T7 through the first red blood cell path T6 (the first branched path T6a).

A step of diluting the red blood cells (a step of diluting) is performed. Specifically, the sixth pump P6 is driven. Consequently, the diluent containing riboflavin is flown from the diluent storing section 15 to the diluting path T7. Then, in the diluting path T7, the concentrated red blood cells are diluted in the diluent containing riboflavin.

A step of emitting UV to the red blood cells (a step of inactivating viruses in a blood component, a step of inactivating viruses in red blood cells) is performed. Specifically, the concentrated red blood cells having been diluted are flown into the UV emitting unit 16 through the diluting path T7. Then, the UV emitting unit 16 emits UV light to the concentrated red blood cells, so as to perform the virus inactivation process.

According to the present embodiment, in the diluting path T7 of the diluting section, the concentrated red blood cells resulting from the separation performed by the blood component separation section 12A of the centrifuge 12 is diluted in the diluent containing riboflavin in the above manner. This reduces the concentration of the concentrated red blood cells. Then, the UV emitting unit 16 performs the virus inactivation process by emitting UV light to the concentrated red blood cells thus diluted to a lower concentration.

Since the concentrated red blood cells are first diluted in the diluent containing riboflavin in the above manner so that the concentration of the concentrated red blood cells is reduced, a space between individual red blood cells in the concentrated red blood cells increases. Thus, when UV light is emitted to the concentrated red blood cells, the UV light is hardly absorbed in or reflected by the red blood cells. This makes it easier for the UV light to be transmitted through the concentrated red blood cells, thereby making it easier for riboflavin contained in the concentrated red blood cells to be irradiated with the UV light. This enhances efficiency in the process of inactivating viruses in the concentrated red blood cells. Therefore, it is possible to quickly perform the virus inactivation process on the concentrated red blood cells.

Note that increasing a dilution rate of the concentrated red blood cells results in an increase in the efficiency of the virus inactivation process. For example, if the dilution rate of the concentrated red blood cells is doubled, the efficiency in the virus inactivation process is also doubled. In this case, time taken to perform the virus inactivation process on the concentrated red blood cells is reduced to half.

Furthermore, according to the present embodiment, the above-described virus inactivation process on concentrated red blood cells and the process of separating and collecting concentrated red blood cells can be performed as a series of processes in the blood component separation device 1. Thus, the present embodiment can omit a troublesome traditional procedure of performing, by use of another dedicated device, a virus inactivation process on a red blood cell product resulting from separation and collection performed by a blood component separation device. This improves a working efficiency in the process of separating and collecting concentrated red blood cells and the virus inactivation process on the concentrated red blood cells.

Figure 6:
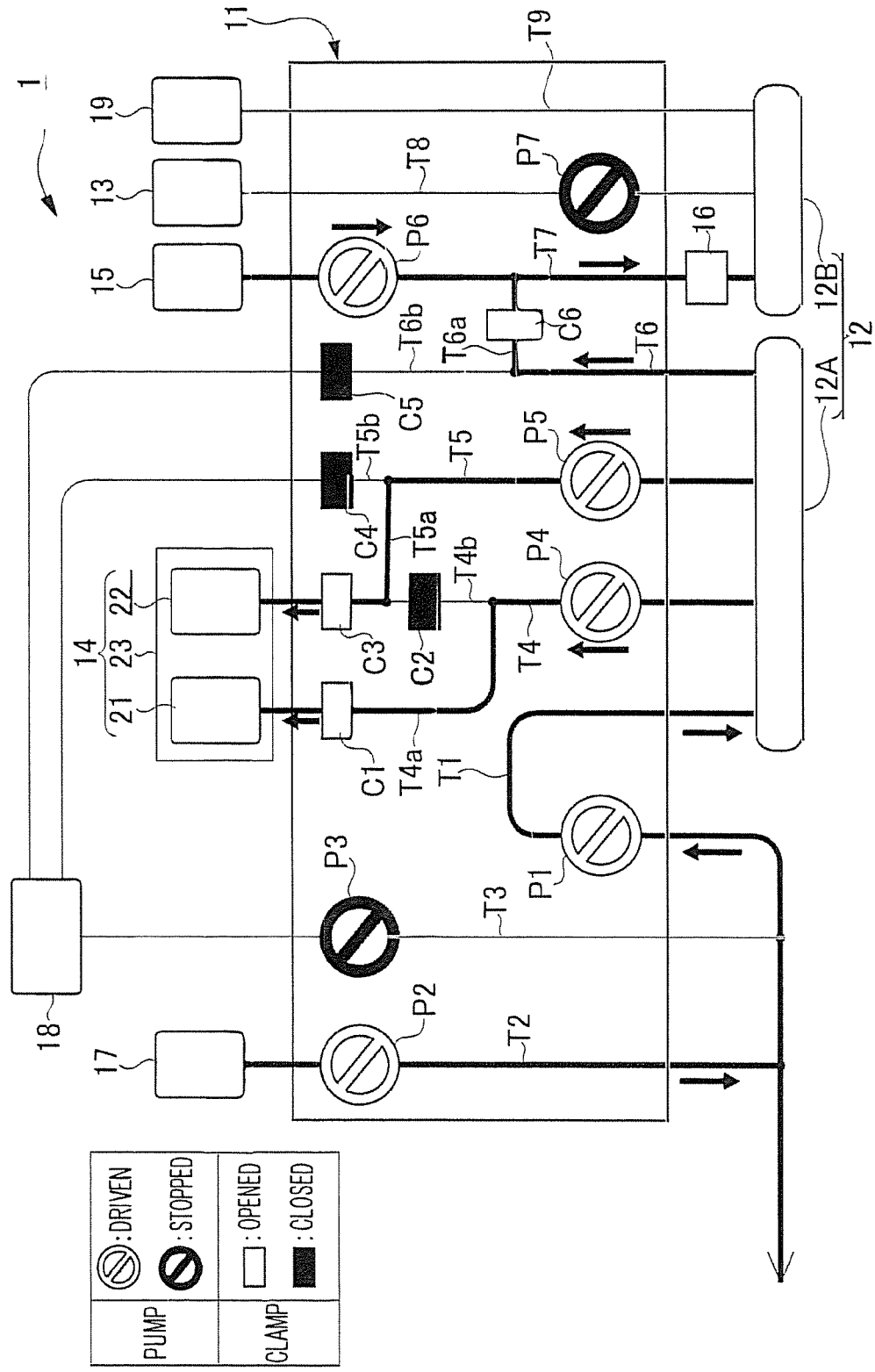
FIG. 6 is a view illustrating a step of collecting platelets and a step of emitting UV to the platelets, in addition to the steps shown in FIG. 5.

Next, a step of collecting the platelets is performed. Specifically, as shown in FIG. 6, the fourth clamp C4 is closed, and the third clamp C3 is opened. This allows the platelets separated from the blood as a result of the centrifugation performed by the blood component separation section 12A of the centrifuge 12 to be collected into the platelet collecting bag 22 through the platelet path T5 (first branched path T5a).

A step of emitting UV to the platelets (a step of inactivating viruses in the platelets) is performed. Specifically, the UV emitting unit 23 emits UV light to the platelets (concentrated platelet solution) collected in the platelet collecting bag 22, so as to perform the virus inactivation process. This yields the platelets having been subjected to the virus inactivation process. As described above, the platelet collecting bag 22 preliminarily contains riboflavin. Thus, the virus inactivation process can be performed effectively.

Next, a step of adjusting a concentration of the red blood cells is performed. Specifically, concentration adjustment is performed on the concentrated red blood cells having been diluted to a lower concentration and having been subjected to the virus inactivation process in the above-described manner. Specifically, the concentrated red blood cells are centrifuged by the condenser 12B in the above-described manner, so that a concentration of the concentrated red blood cells is adjusted to a desired concentration.

Figure 7:
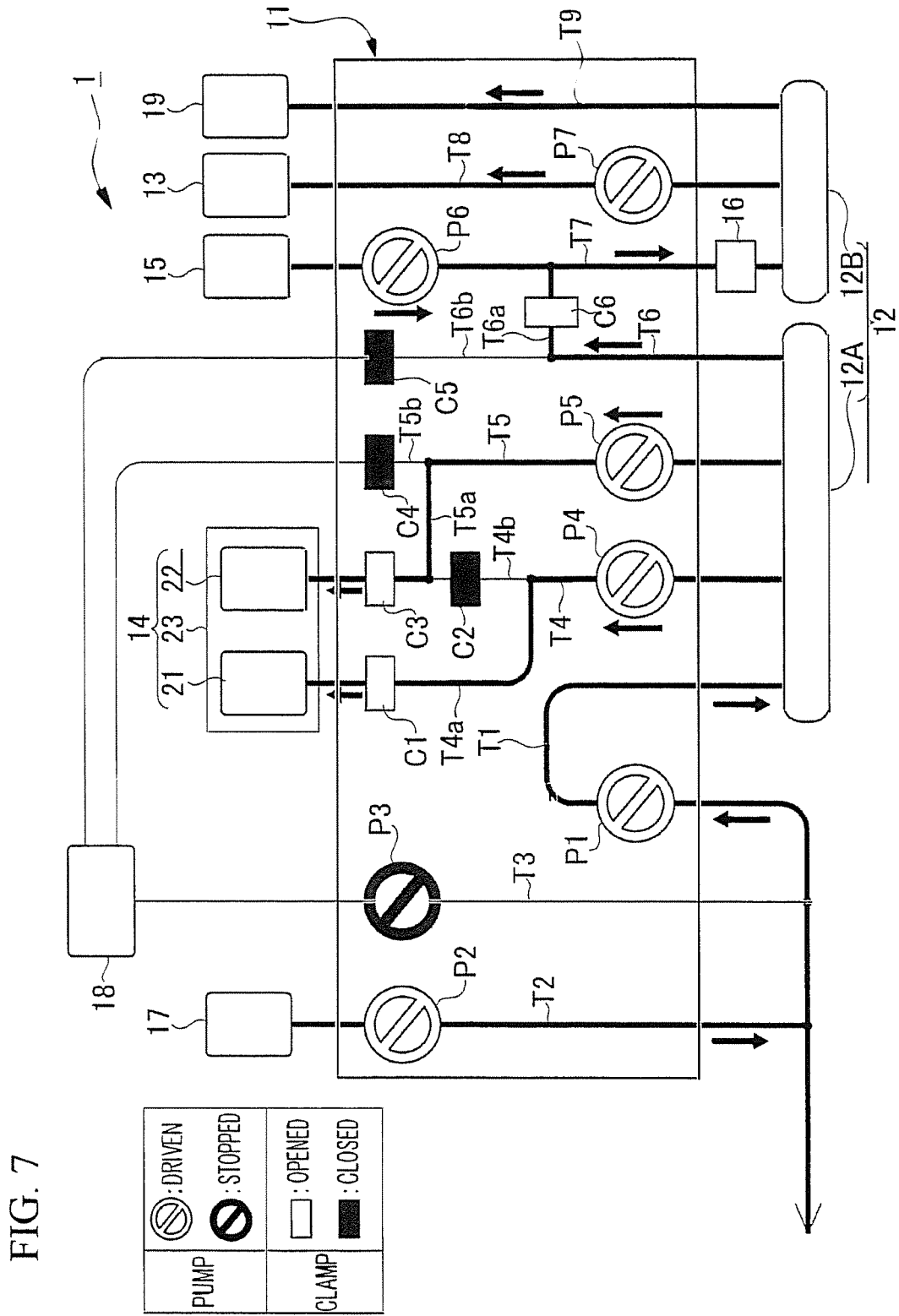
FIG. 7 is a view illustrating a step of adjusting a concentration of the red blood cells, in addition to the steps shown in FIG. 6.

Then, as shown in FIG. 7, the seventh pump P7 is driven, so that the concentrated red blood cells whose concentration has been adjusted are collected into the red blood cell collecting bag 13 through the second red blood cell path T8. Consequently, it is possible to obtain the concentrated red blood cells whose concentration has been adjusted to a desired concentration. The red blood cell preservation solution separated and removed by the condenser 12B is collected into the fluid waste bag 19 through the fluid waste path T9 as fluid waste.

Figure 8:
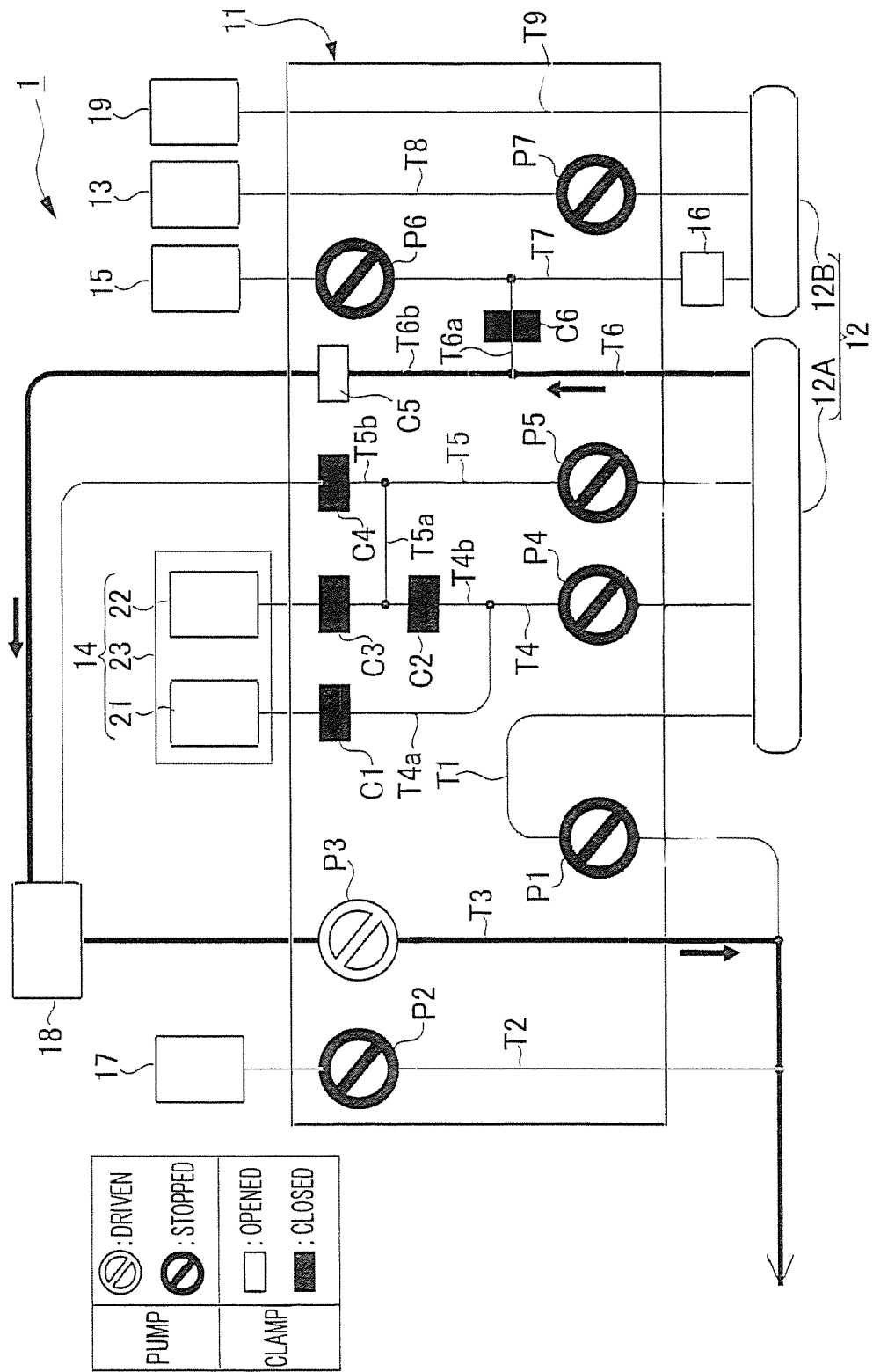
FIG. 8 is a view illustrating a step of returning the blood.

Next, upon completion of the collection of the various blood components, a step of returning the blood is performed. Specifically, as shown in FIG. 8, the first clamp C1, the third clamp C3, and the sixth clamp C6 are closed, and the fifth clamp C5 is opened. Furthermore, the first pump P1, the second pump P2, the fourth pump P4, the fifth pump P5, the sixth pump P6, and the seventh pump P7 are stopped, and the third pump P3 is driven. This allows the blood to be returned from the blood component separation section 12A of the centrifuge 12 to the blood donor through the first red blood cell path T6 (the second branched path T6b), the reservoir 18, and the blood returning path T3.

As described above, the blood component separation device 1 of the present embodiment includes: the blood component separation section 12A, provided in the centrifuge 12, for separating a blood component from blood by centrifuging the blood, where the blood has been collected from a blood donor; the diluting section (the diluent storing section 15, the diluting path T7, and the sixth pump P6) for diluting, in the diluent containing riboflavin, concentrated red blood cells separated by the blood component separation section 12A; and the UV emitting unit 16 for performing the virus inactivation process by emitting UV light to the concentrated red blood cells thus diluted.

As such, according to the blood component separation device 1 of the present embodiment, after the concentrated red blood cells are separated from the blood, the concentrated red blood cells are diluted in the diluent containing riboflavin, so that a concentration of the concentrated red blood cells is reduced. This makes it easier for riboflavin to be irradiated with UV light, when the UV light is emitted to the concentrated red blood cells. Consequently, viruses in the concentrated red blood cells are more likely to be inactivated. Thus, with the blood component separation device 1 of the present embodiment, it is possible to perform the virus inactivation process on the concentrated red blood cells separated from the blood and to reduce time taken to perform the virus inactivation process.

Furthermore, the virus inactivation process on the concentrated red blood cells and the process of separating and collecting the concentrated red blood cells can be performed as a series of processes in the blood component separation device 1. This improves a working efficiency in the process of separating and collecting the concentrated red blood cells and the virus inactivation process on the concentrated red blood cells.

Moreover, the blood component separation device 1 of the present embodiment includes the condenser 12B for adjusting a concentration of the concentrated red blood cells having been subjected to the virus inactivation process. With this, the concentrated red blood cells that have been once diluted to a lower concentration can be collected after adjusted to a desired concentration.

The condenser 12B of the present embodiment adjusts a concentration of the concentrated red blood cells by centrifuging the concentrated red blood cells. This allows the red blood cell preservation solution to be separated and removed from the concentrated red blood cells having been diluted by application of a centrifugal force thereto. Therefore, it is possible to easily collect the concentrated red blood cells having a desired concentration.

Furthermore, the blood component separation section 12A and the condenser 12B of the present embodiment are provided in the single centrifuge 12. Thus, by driving the centrifuge unit 31 so as to be rotated, the process of separating the blood component and the process of adjusting a concentration of the concentrated red blood cells can be performed at once. This reduces time taken to collect, from the blood, the concentrated red blood cells having a desired concentration. Furthermore, since the single centrifuge unit 31 can serve as a driving section used for the process of separating the blood component and for the process of adjusting a concentration of the concentrated red blood cells, the blood component separation device 1 can be miniaturized.

The blood component separation device 1 of the present embodiment includes the UV emitting unit 23 for performing the virus inactivation process on plasma and platelets separated by the blood component separation section 12A. Thus, it is possible to collect the plasma and the platelets having been subjected to the virus inactivation process, in addition to the concentrated red blood cells having been subjected to the virus inactivation process in the above-described manner.

Figure 9:
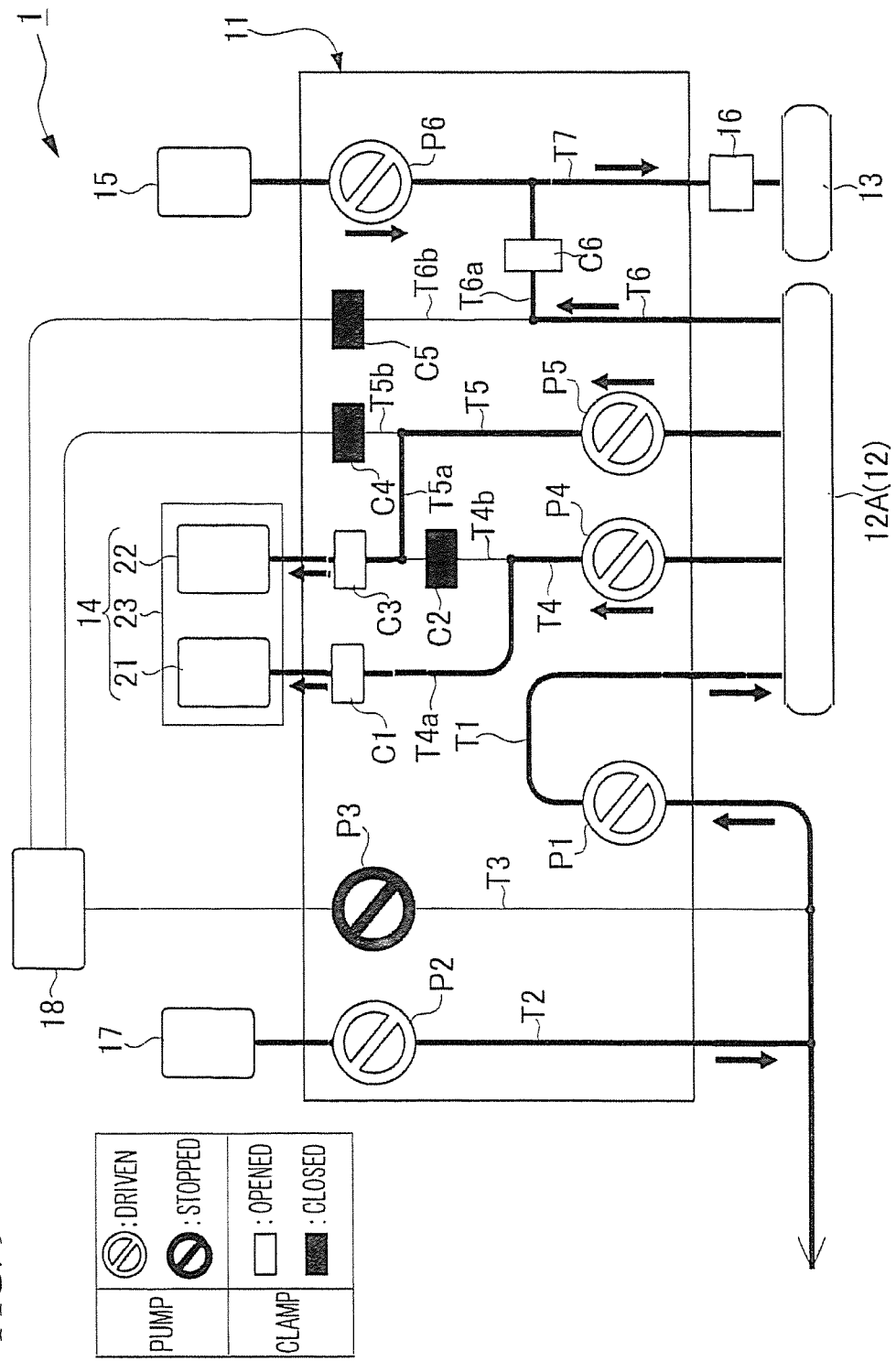
FIG. 9 is a view schematically illustrating a configuration of a blood component separation device according to a first variation.

Meanwhile, a variation as below is possible. As shown in FIG. 9, first, a blood component separation device 1 of a first variation includes a diluting path T7 connected to a red blood cell collecting bag 13 rather than to a condenser 12B, to which the diluting path T7 of the foregoing embodiment is connected. The blood component separation device 1 of the first variation does not include a second red blood cell path T8, a fluid waste path T9, a seventh pump P7, or a fluid waste bag 19. In the blood component separation device 1 of the first variation configured as above, concentrated red blood cells having been diluted and having been subjected to a virus inactivation process are collected into a red blood cell collecting bag 13 through the diluting path T7. Then, the red blood cell collecting bag 13 is centrifuged by another centrifugal separator, and a red blood cell preservation solution, which appears as a supernatant, is removed. In this manner, a concentration of the concentrated red blood cells is adjusted.

Figure 10:
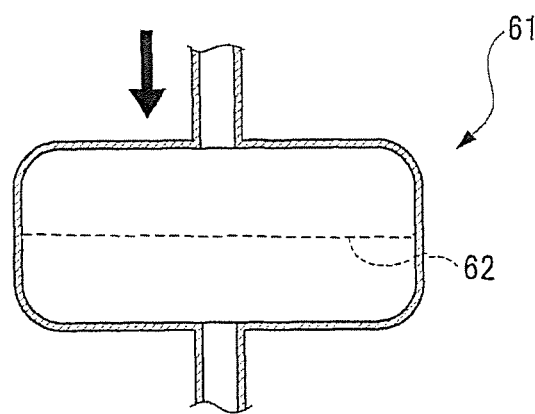
FIG. 10 shows a state where concentrated red blood cells are not flown to a filter yet in a concentration adjustment section according to a second variation.
Figure 11:
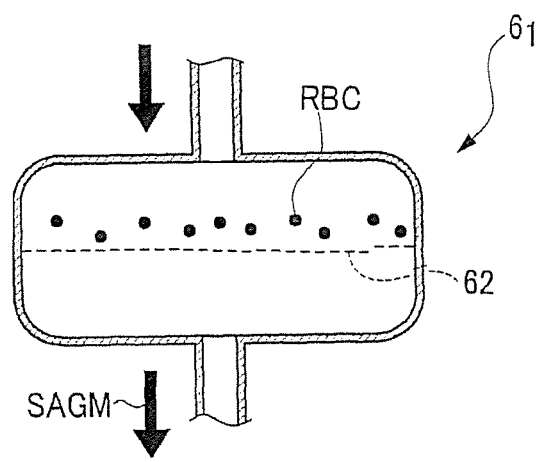
FIG. 11 shows a state where the concentrated red blood cells are flown to the filter in the concentration adjustment section according to the second variation.
Figure 12:
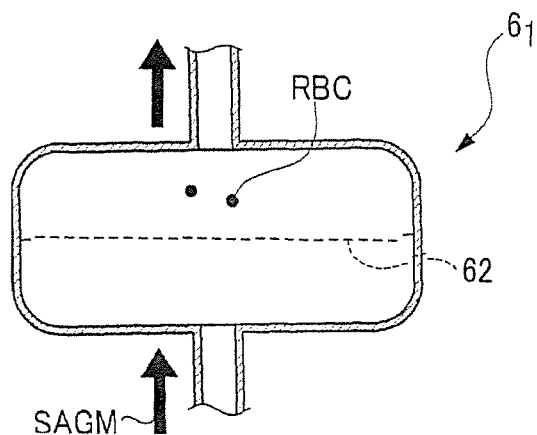
FIG. 12 shows a state where a red blood cell preservation solution removed from the concentrated red blood cells is flown in an opposite direction in the concentration adjustment section according to the second variation.

A blood component separation device 1 of a second variation includes a concentration adjustment section 61 as those shown in FIGS. 10 to 12, instead of the condenser 12B. The concentration adjustment section 61 includes a filter 62. The concentration adjustment section 61 is connected to a red blood cell collecting bag 13 shown in FIG. 9. The concentration adjustment section 61 adjusts a concentration of concentrated red blood cells to a desired concentration in the following manner. That is, the concentrated red blood cells are flown to the filter 62 from the red blood cell collecting bag 13, so that a red blood cell preservation solution SAGM (liquid component) is removed from the concentrated red blood cells and red blood cells RBC are caught by the filter 62. After that, a predetermined amount of the red blood cell preservation solution SAGM thus removed is flown to the filter 62 in an opposite direction, so that the red blood cells RBC thus caught by the filter 62 are collected in the red blood cell collecting bag 13. With this, the concentrated red blood cells that have been once diluted to a lower concentration can be collected after adjusted to a desired concentration.

In another variation, a UV emitting unit 23 may perform a virus inactivation process on only either one of plasma and platelets. In further another variation, a blood component separation device 1 may include a diluting section and a platelet virus inactivation section. The diluting section dilutes, in a diluent containing riboflavin, platelets separated by the blood component separation section 12A. The platelet virus inactivation section performs a virus inactivation process by emitting UV light to the platelets having been diluted.

Note that the above-described embodiments are merely examples, and by no means limit the present disclosure, and, needless to say, can be improved or varied in many ways within the scope of a gist of the present disclosure.

REFERENCE SIGNS LIST

1 Blood component separation device
11 Cassette
12 Centrifuge
12A Blood component separation section
12B Condenser
13 Red blood cell collecting bag
14 Plasma and platelet collecting section
15 Diluent storing section
16 UV emitting unit
19 Fluid waste bag
21 Plasma collecting bag
22 Platelet collecting bag
23 UV emitting unit
31 Centrifuge unit
32 Flow Path
32a Inlet
32b Accumulation chamber
33 Inflow line
34 First red blood cell line
35 Platelet and while blood cell line
36 Chamber
37 Platelet line
38 Plasma line
51 Path
51a Inlet
51b Accumulation chamber
52 Inflow line
53 Second red blood cell line
54 Fluid waste line
61 Concentration adjustment section
62 Filter
T1 Whole blood path
T2 Anticoagulant path
T3 Blood returning path
T4 Plasma path
T4a First branched path
T4b Second branched path
T5 Platelet path
T5a First branched path
T5b Second branched path
T6 First red blood cell path
T6a First branched path
T6b Second branched path
T7 Diluting path
T8 Second red blood cell path T9 Fluid waste path
P1 to P7 First pump to seventh pump
C1 to C6 First clamp to sixth clamp
L Central line
RBC Red blood cells
WBC White blood cells
PLT Platelets
PPP Plasma
SAGM Red blood cell preservation solution

The invention claimed is:

1. A blood component separation device, the device comprising:
    a centrifugal separation device;
    a blood component separation section configured to separate a blood component from blood by centrifugation;
    a diluting section configured to dilute, in a diluent containing a photoactive virus inactivation agent, the blood component separated by the blood component separation section;
    a blood-component virus inactivation section configured to perform a virus inactivation by exposing the diluted blood component to a UV light source; and
    a concentration adjustment section,
    wherein the blood component separation section and the concentration adjustment section are disposed within the centrifugal separation device.

2. The blood component separation device according to claim 1, wherein the concentration adjustment section is configured to adjust a concentration of the blood component that has been subjected to the virus inactivation process.

3. The blood component separation device according to claim 2, wherein the concentration adjustment section adjusts the concentration of the blood component by centrifuging the blood component.

4. The blood component separation device according to claim 3, wherein the blood component separation section and the concentration adjustment section are provided in a same centrifugal separation section of the centrifugal separation device.

5. The blood component separation device according to claim 2, wherein the concentration adjustment section includes a filter, and
    wherein the concentration of the blood component is adjusted by flowing the blood component into the filter in one direction to catch the blood component in the filter, and then flowing a liquid component in an opposite direction across the filter to collect the blood component.

6. The blood component separation device according to claim 1, wherein the blood component is concentrated red blood cells.

7. The blood component separation device according to claim 1, wherein the blood component is platelets.

8. The blood component separation device according to claim 6, further comprising a plasma virus inactivation section configured to perform a virus inactivation process on plasma separated by the blood component separation section.

9. The blood component separation device according to claim 6, further comprising a platelet virus inactivation section configured to perform a virus inactivation process on platelets separated by the blood component separation section.

10. A blood component separation method, the method comprising:
    separating a blood component from blood by centrifugation;
    diluting, in a diluent containing a photoactive virus inactivation agent, the separated blood component;
    performing a virus inactivation by exposing the diluted blood component to a UV light; and
    adjusting a concentration of the blood component subjected to UV light,
    wherein the separating of the blood component from blood and the adjusting of the concentration of the blood component subjected to UV light occur in a single centrifugal separation device.

11. The method of claim 10, wherein the adjusting of the concentration of the blood component subjected to UV light is performed using a filter.

12. The method of claim 10, wherein the separating of the blood component from blood and the adjusting of the concentration of the blood subjected to UV light are provided in a same centrifugal separation section of centrifugal separation device.

* * * * *